United States Patent [19]

Heckmann et al.

[11] Patent Number: 4,800,067
[45] Date of Patent: Jan. 24, 1989

[54] DEVICE FOR DETECTING GASES WHICH MUST BE TREATED BEFORE TESTING

[75] Inventors: Johannes Heckmann, Luebeck; Wolfgang May, Reinfeld, both of Fed. Rep. of Germany

[73] Assignee: Dragerwerk Aktiengesellschaft, Fed. Rep. of Germany

[21] Appl. No.: 69,386

[22] Filed: Jul. 2, 1987

[30] Foreign Application Priority Data

Jul. 24, 1986 [DE] Fed. Rep. of Germany ....... 3625085

[51] Int. Cl.⁴ .................... G01N 21/05; G01N 21/78
[52] U.S. Cl. ...................... 422/86; 422/103; 422/85
[58] Field of Search .................. 422/58, 59, 60, 61, 422/86, 103, 85; 436/132

[56] References Cited

U.S. PATENT DOCUMENTS 3,459,508  8/1969  Miczka ................................ 422/85
4,329,318  5/1982  Le Grouyellec et al. ............ 422/59

FOREIGN PATENT DOCUMENTS 2854628  6/1980  Fed. Rep. of Germany ........ 422/86

Primary Examiner—Barry S. Richman
Assistant Examiner—Timothy M. McMahon
Attorney, Agent, or Firm—McGlew and Tuttle

[57] ABSTRACT

A test tube with several reagent layers affecting the detection reaction, which are separated from one another by means of a permeable interlayer, is improved so that an undesired exchange of reaction products or reagents between the layers is prevented during the measurement process and also during the dwell time, i.e. before and after the measurement. To this end, the interlayer is provided with a valve unit that opens only during the flow.

4 Claims, 1 Drawing Sheet

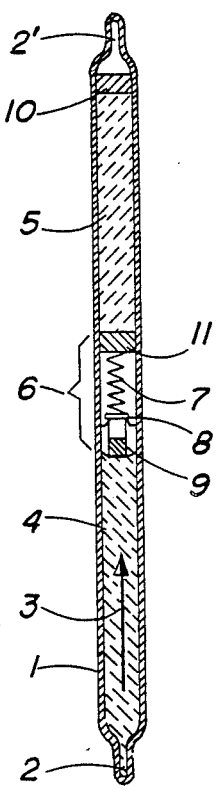

DEVICE FOR DETECTING GASES WHICH MUST BE TREATED BEFORE TESTING

FIELD AND BACKGROUND OF THE INVENTION

This invention relates in general to gas or pollutant testing devices and in particular to a new and useful device for detecting gases which must first be treated to form reaction products that lead to a distinct color in a following indicator material.

This invention particularly concerns a test tube with several reagent layers affecting the detection reaction, that are separated from one another by a permeable interlayer.

Test tubes with several reagent layers are used particularly for cases in which the successive layers bring about a stepwise reaction of the pollutant to be detected until a colorimetric evaluation is ultimately made accessible in an indicator layer, and also to test tubes in which the degree of color of the indictor layer is compared with a color comparison layer and is thus evaluated.

To detect various gaseous pollutants, it is necessary to convert them first in a preliminary layer into reaction products that lead to a distinct color in a following indicator layer. A test tube of this type has been disclosed by German Patent Application Disclosure No. 27 54 638.

To detect aerosols, gases, and vapors, such as hydrogen chloride, hydrogen fluoride, or sulfur dioxide, reaction products are produced in the preliminary layer that lead to a color in the following layer with known reagents for these reaction products.

To achieve a reliable indication of a color, the reaction products from the preliminary layer triggering the coloration must be gaseous. However, this also makes possible unhindered diffusion of the reaction products into the indicator layer, so that residual amounts of volatile components from the preliminary layer still pass over into the reagent layer even after completion of the measurement, and can thus subsequently distort the coloration in the indicator layer or even reverse it. For example, a preliminary layer impregnated with chromosulfuric acid and an indicator layer with an acid indicator (for example, Bromphenol Blue) are used to detect vinyl chloride. Hydrochloride acid is formed with the chromosulfuric acid under the action of the vinyl chloride, which leads to a coloration with the Bromphenol Blue in the indicator layer. Vinyl chloride also forms other decomposition products, such as chromyl chloride, with sulfuric acid. After completing the measurement, this chromyl chloride would diffuse through the porous interlayer into the indicator layer and lead to an additional coloration. The sulfuric acid of the preliminary layer can also withdraw from the reagent system the hydrochloric acid formed in the indicator layer, and thereby cause unstable behavior of the color after it is formed. It is then no longer possible to make a clear correlation between the degree of coloration and the amount of pollutant detected.

If the flow of the pollutant through the test tube is produced by a discontinuous pumping process from several individual pump strokes, diffusion of the components from the preliminary layer into the reagent layer must also be prevented n the period between the strokes. For example, if a test tube is to be used for the detection of methylene chloride, the preliminary layer is composed of potassium dichromate with concentrated sulfuric acid, impregnated on a carrier. The indicator layer includes palladium salt dissolved in water, that is also impregnated on a carrier. The methylene chloride is converted into carbon monoxide in the preliminary layer, which colors the palladium salt. The volatile water fraction must also not diffuse back into the preliminary layer during the dwell time between the successive pump strokes, since the concentrated sulfuric acid would become so very dilute that a reliable reaction of the pollutant to be detected to form carbon monoxide in the preliminary layer would be prevented.

When using the known system of preliminary layer and indicator layer, it is therefore impossible to achieve a reliable coloration of the indicator layer in all applications.

SUMMARY OF THE INVENTION

The invention provides a test tube in which an undesired exchange of reaction products or reagents between the layers is prevented during the measurement process and also during the dwell time, i.e., before and after the measurement.

This problem is solved by providing the interlayer with a valve element that opens only during the flow. Such a valve element opens the path for the reaction products from the preliminary layer into the indicator layer only as long as a flow through the test tube is produced. Undesired diffusion of reaction products or reagent components between the preliminary layer and the indicator layer is prevented.

In a desirable refinement of the invention, the valve element comprises a spring-loaded disk valve. This then acts in a simple way as a check valve.

In order to use a few movable parts as possible with as small a structural size as possible, the valve element is advantageously composed of a slitted elastic disk held between retaining units.

Another favorable refinement of the invention includes a valve unit in the form of a spring-loaded ball valve.

Accordingly it is an object of the invention to provide an improved device for testing gases for pollutants which includes a test tube which is openable at each end to permit flow through the tube in a direction which would pass the gas first through a reaction layer so as to produce reaction products that lead to a distinct color in a following indicator layer and with a valve between the layers which closes when there is no flow through the tube.

A further object of the invention is to provide a device for testing gas which is simple in design rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only figure of the drawing is an axial sectional view of a testing tube for detecting gases constructed in accordance with the invention.

DESCRIPTION OF THE PREFERRED EMBODIMENT

Referring to the drawings in particular the invention embodied therein comprises a device for detecting gases which must be treated before testing in which comprises a test tube 1 having an inflow which is effective by breaking a frangible tip 2 at one end of the tube and an outflow to the opposite end at the frangible tip 2'.

In accordance with the invention the gas which is directed through the tube in a direction of the arrow 3 is changed by a preliminary or reaction layer 4 to reaction products that lead to a distinct color in a following indicator in an indicating layer 5. In accordance with the invention a separate chamber is provided for an interlayer 6 having a valve disk 8 which is biased by a helical spring 7 into a closed position to close off the layer 4 from the layer 5 when there is no flow through the tube.

The single figure shows a test tube 1 with two fragile tips 2, which has a preliminary layer 4 and an indicator layer 5 in the flow direction shown by the arrow 3. The two layers 4 and 5 are separated from one another by an interlayer 6 of a permeable retainer unit 11 and another retainer unit 9 designed as a valve seat, and the valve disk 8 and helical spring 7 between them. The valve plate 8, for example in the form of a mico sheet, is pressed by the spring 7 against the seat 9. The indicator layer 5 is held in position toward the tip 2 with a plug 10.

When the tips 2 are broken off, the test tube 1 is flushed with a stream in the direction of the arrow 3. During the flow, the valve plate 8 lifts from the seat 9 and thus opens the path for the reaction products formed in the preliminary layer 4 into the indicator layer 5. When the flow in interrupted, for example because of individual successive pump strokes, the valve element 8 and 9 closes the diffusion path between the preliminary layer 4 and the indicator layer 5. Even after the measurement is completed with the tips 2 opened, no diffusion exchange takes place between volatile components from the preliminary layer 4 and the indicator layer 5.

What is claimed is:

1. Gas testing device comprising a transparent tube having breakable tips at each end, which when broken, define an inlet and an outlet at the respective ends of said tube, a plurality of different material layers for detecting gases arranged in said tube in succession, at least two spacedapart retainer elements arranged between at least two of said material layers of different material and defining a valve space between said layers, one of said retainer elements being gas-permeable and the other of said retainer elements defining a communication passage between said valve space and an adjacent one of said layers of different materials, said communication passage having a closeable valve seat, a valve member in said valve space engageable with said valve seat and forming a valve therewith to close said passage, and biasing means biasing said valve member on said seat, said valve being openable when there is a gas flow through said tube in a direction opposite to said biasing means and being closeable by said biasing means to close off said passage in the communication between said layers of different material.

2. A gas testing device according to claim 1, wherein one of said plurality of layers of different material comprises a reaction material and an adjacent layer of material comprises an indicator material which are separated by said valve space.

3. A gas testing apparatus comprising:
a transparent tube having a first end and a second end, said first end and said second end adapted to form and inlet and an outlet of said tube respectively for testing gas flowing in a flow direction through said inlet and exiting through said outlet;
at least one layer of material which reacts with gas to be tested, said material which reacts being positioned within said tube adjacent said inlet end;
a first gas permeable retainer element positioned within said tube adjacent said layer of reaction material;
a second gas permeable retainer element positioned within said tube spaced from said first gas permeable retainer on a side of said gas permeable retainer element opposite the side occupied by said at least one layer of reaction material;
a layer of indicating material positioned within said tube on a side of said second gas permeable retainer element opposite the side occupied by said first gas permeable retainer element and adjacent said outlet end;
valve means positioned between said first gas permeable retainer element and said second gas permeable retainer element, said valve means including a valve seat associated with said first gas permeable retainer element, a valve plate adapted to engage said valve seat and spring element positioned between said second gas permeable retainer element and said valve plate, said spring element having a biasing force urging said valve plate into engagement with said valve seat, said valve means for preventing fluid flow between said layers in either said flow direction, or in a direction opposite to said flow direction, and for allowing fluid flow between said layers when there is a flow through said tube acting on said valve plate opposite said biasing force.

4. A gas testing apparatus comprising:
a transparent tube having breakable tips at each end, which when broken, define an inlet and an outlet of said tubes for testing gas flowing in a flow direction through said inlet and exiting through said outlet;
at least one preliminary layer of reacting material to convert the gas to be tested into reaction products, said at least one preliminary layer of reacting material being positioned within said tube adjacent said inlet end;
a first gas permeable retainer element positioned within said tube adjacent said at least one preliminary layer of reacting material;
a second gas permeable retainer element positioned with said tube spaced from said first gas permeable retainer element on a side of said first gas permeable retainer element opposite the side occupied by said at least one preliminary layer of reacting material;
a layer of indicating material positioned within said tube on a side of said second gas permeable retainer element opposite the side occupied by said first gas permeable retainer element and adjacent said outlet end, the presence of the reaction products from said at least one preliminary layer of reacting material triggering a visual indication in said indicating layer; and, valve means positioned between said first gas permeable retainer element and said second gas permeable retainer element for preventing fluid flow between said layers in either said flow direction or in a direction opposite to said flow direction, and for allowing fluid flow between said layers when there is a gas flow through said tube in said flow direction.

* * * * *